(12) United States Patent
Cherek et al.

(10) Patent No.: US 7,433,503 B2
(45) Date of Patent: Oct. 7, 2008

(54) METHOD AND ARRANGEMENT FOR POSITIONING A PATIENT IN A MEDICAL DIAGNOSIS OR THERAPY DEVICE

(75) Inventors: Dieter Cherek, Hirschaid (DE); Robert Kagermeier, Nürnberg (DE); Michael Loser, Erlangen (DE); Donal Medlar, Weisendorf (DE); Hendrik Steinmann, Worms (DE); Uwe Urmoneit, Gerhardshofen (DE)

(73) Assignee: Siemens Aktiengesellschaft, Munich (DE)

( * ) Notice: Subject to any disclaimer, the term of this patent is extended or adjusted under 35 U.S.C. 154(b) by 819 days.

(21) Appl. No.: 10/622,519

(22) Filed: Jul. 18, 2003

(65) Prior Publication Data

US 2004/0081341 A1    Apr. 29, 2004

(30) Foreign Application Priority Data

Jul. 18, 2002    (DE) ................................ 102 32 676

(51) Int. Cl.
- *G06K 9/00* (2006.01)
- *G21K 1/12* (2006.01)
- *A61B 6/00* (2006.01)

(52) U.S. Cl. .......................................... 382/128; 378/4
(58) Field of Classification Search ......... 382/128–140; 378/4–20
See application file for complete search history.

(56) References Cited

U.S. PATENT DOCUMENTS

| | | | | |
|---|---|---|---|---|
| 4,411,012 A | * | 10/1983 | Pfeiler et al. .................. 378/17 |
| 4,609,940 A | * | 9/1986 | Born et al. .................. 378/98.5 |
| 4,773,086 A | * | 9/1988 | Fujita et al. .................. 378/4 |
| 5,222,499 A | * | 6/1993 | Allen et al. .................. 600/426 |
| 5,526,814 A | | 6/1996 | Cline et al. |
| 5,603,318 A | | 2/1997 | Heilbrun et al. |
| 5,622,187 A | * | 4/1997 | Carol .................. 128/897 |
| 5,848,114 A | * | 12/1998 | Kawai et al. .................. 378/4 |
| 6,196,715 B1 | * | 3/2001 | Nambu et al. .................. 378/11 |
| 6,405,072 B1 | * | 6/2002 | Cosman .................. 600/426 |
| 6,674,449 B1 | * | 1/2004 | Banks et al. .................. 715/740 |
| 6,901,130 B2 | | 5/2005 | Bruder et al. |
| 2001/0016684 A1 | | 8/2001 | Shahidi |
| 2002/0118280 A1 | | 8/2002 | Medlar et al. |
| 2003/0053667 A1 | * | 3/2003 | Paragios et al. ............. 382/128 |
| 2003/0100998 A2 | * | 5/2003 | Brunner et al. ............. 702/19 |

FOREIGN PATENT DOCUMENTS

| | | |
|---|---|---|
| DE | 195 08 715 | 9/1996 |
| DE | 19508715 A1 * | 9/1996 |
| JP | 08257024 A * | 10/1996 |
| WO | WO 00/15114 | 3/2000 |

OTHER PUBLICATIONS

Baxes, Gregory A. Digital Image Processing: Principles and Applications: 1994. John Wiley & Sons, Inc. pp. 335-337.*

* cited by examiner

*Primary Examiner*—Bhavesh Mehta
*Assistant Examiner*—Manav Seth
(74) *Attorney, Agent, or Firm*—Schiff Hardin LLP (57) ABSTRACT

In a method and a device for positioning a patient in a medical diagnosis device or therapy device, an image-recording device records an image of the patient, which is displayed on a screen, and an image processor aids the positioning of the patient. At least one body region is automatically detected by the image processor, and a scan area is automatically suggested on the screen that covers the body region.

26 Claims, 6 Drawing Sheets

METHOD AND ARRANGEMENT FOR POSITIONING A PATIENT IN A MEDICAL DIAGNOSIS OR THERAPY DEVICE

BACKGROUND OF THE INVENTION

1. Field of the Invention

The present invention concerns a method and an arrangement for positioning a patient in a medical diagnosis device or therapy device (medical device) of the type having a unit that interacts with the patient, a computer, and a patient bed that can be adjusted in at least one plane, and at least one image-recording device that acquires an image of the exterior of the patient and displays it on a screen, and an image processor that supervises or controls the positioning of the patient, wherein the computer "knows" the spatial correlation between the coordinate system of the treatment unit and the image-recording device.

2. Description of the Prior Art

A method and arrangement of the above general type are known from German published application 195 08 715. A medical diagnosis device with a method for positioning a patient in this diagnosis device is described in this application, wherein an image-recording device detects and localizes, by image processing, a marking applied to the patient before the imaging, such that a spatial correlation between the detected position of the patient and the coordinate system of the diagnosis device can be established, and the patient bed is subsequently automatically moved into a desired position. It is problematic that a marking first must be applied on the patient by the treating physician or appropriately trained medical personnel. The application of such markings to the patient can be undesirable for various reasons, so that this method and the corresponding device are not suitable in every situation.

Another similar method and a similar device are known from the German published application 101 09 219, corresponding to co-pending United States co-pending application Ser. No. 10/081,225 field Feb. 22, 2002 and published as Pub. No. 2002/0118280 (both publications occurring after the priority date of the present application). An imaging diagnosis system with a positioning device is described, wherein an image of the patient on the patient bed is acquired by at least one image-recording device and the image is displayed on a monitor. The operating personnel can manually select the desired examination region in the image on the screen with a region selection device, by the operator designating the desired examination region (for example, with a mouse or with a touch screen) with a drawn rectangle. On the basis of the indicated scan area, the positioning device subsequently guides the patient in the diagnosis system to the desired position and implements the examination in this region.

Such a procedure requires a very good training of the operating personnel, since it is expected that the operator can correctly convert the medical specifications into the correct scan area, which is then entered as an input. This method is also susceptible to error in the form of individual input error. Moreover, since the input is dependent on the individual operating person, different actual scan areas for examination of the same diagnostic region can be entered from different operating personnel.

Furthermore, it is commonly known that positioning of the patient by means of light or laser beam localizers is available as an alternative to the positioning devices and positioning methods that are based on a topogram (exterior image). In such techniques, the indication of the length of the scan area is shown by light markings, such that the operation makes the corresponding adjustment of the scan area directly on the patient.

In all of the cases cited above, a manual, time-consuming, and less-than-satisfactory interaction is required on the part of the operating personnel, which is regarded as disadvantageous, particularly in survey examinations. If topogram recordings are produced in addition to exact positionings, it results in an increased stress on the patient that should likewise be avoided.

SUMMARY OF THE INVENTION

It is an object of the present invention to provide a method that can be implemented simply, and which also enables personnel with less training, to record with fewer operations the desired body region to be examined or to be treated, and to determine the corresponding scan area, whereby an additional topogram recording should be foregone if possible in the implementation. It is also an object of the present invention to provide, a corresponding device for implementation of this simplified method.

The above are achieved in accordance with the invention wherein the individual body regions, are automatically determined by use of a known image analysis of a recording of the exterior a patient on a patient bed, and wherein such an automatic analysis of the image of a patient is employed for the positioning in a diagnosis device or therapy device. The image of a patient on a bed is automatically analyzed, such that an automatic detection of the individual body regions (for example head, abdomen, chest, and extremities) is made, so that individual scan areas can be subsequently determined. In this manner, it is now possible for the operating personnel to set the scan area by means of a simple selection and/or designation of an automatically determined body region. No deeper anatomical knowledge is required on the part of the operating personnel, beyond merely the indication of the desired body regions to be scanned must be made. If these individual body regions are already shown on the screen and, as the case may be, also automatically indicated by the image processor, a mouse click on an appropriate region or touch upon this region on the touch screen is sufficient to automatically arrange the subsequent scan area necessary for this purpose.

IN accordance with the invention in a method for positioning a patient in a medical diagnosis device or therapy device with a treatment unit, a computer, and a patient bed that is adjustable in at least one plane, by recording and displaying of the exterior of the patient, and the positioning of the patient being aided by an image processor, the spatial correlation between the coordinate system of the treatment unit and the image-recording device used to obtain the image is known to the computer. At least one body region is automatically detected by the image processor, and on the screen a scan area is automatically shown that covers this body region.

The diagnosis device or therapy devices can be, for example, an x-ray computed tomography apparatus, a magnetic resonance tomography apparatus, an x-ray angiographic device, or similar nuclear medical diagnosis devices. X-ray or gamma radiation therapy devices and/or lithotriptors, for example, are examples of such therapy devices. The treatment unit is a part of the overall apparatus that interacts with the patient and can include the detectors and/or radiation sources. For example, the scanning unit (gantry) of a computed tomography apparatus as an example of treatment unit. Thus a "treatment unit" need not necessarily render therapy to the patient; it may be a data acquisition unit.

In addition, the image processor can detect at least two different body regions, preferably all body regions detectable in the image, and suggest and indicate a scan area per body region.

The operating personnel must merely choose the desired scan areas or scan area in this case. It can be advantageous for the image processor to optically emphasize the region of the recognized body region. This can ensue, for example, by means of a colored marking or a corresponding brightening or hatching on a black and white monitor.

The selection of a scan area can be effected, for example, via a screen menu or operation of a button.

There is additionally the possibility to manually change the scan area suggested by the image processor, so that possible misinterpretations by the image processor can be corrected.

Furthermore, there is also the option to choose not only a single body region, but also a number of body regions simultaneously, such that a number of body regions are scanned simultaneously in a pass of the patient through the diagnosis device or therapy device.

For example, the scan areas can be set two lines that define the edges of the scan area and are preferably parallel, that can then be correspondingly moved on the screen as necessary to correct the scan area.

The inventive method can be used not only in a single plane with a single image-recording device, but also can be used with two or more image-recording devices having respective recording axes that are independent of one another, preferably orthogonal to each other. It is thus possible to effect not only a 2-dimensional positioning of the patient, but also to position the patient spatially in three dimensions, with in each movement plane of the patient bed having an image-recording device with a recording axis arranged perpendicular to this movement plane. It is possible in this manner to automatically implement a wide range of positioning the patient in 3-dimensional space using at least two image-recording devices. A substantial time savings is achieved due to the automatic determination of the scan area, which is particularly advantageous in the implementation of survey examinations.

Corresponding to the inventive method described above, the above object also is achieved in a device to position a patient in a medical diagnosis device or therapy device which has a treatment unit, a computer, and a patient bed that can be adjusted in at least one plane, wherein at least one image-recording device is provided for the patient that graphically images the patient on a screen and has an image processor to aid the positioning of the patient, and wherein information about the spatial correlation between the coordinate system of the treatment unit and the minimum one image-recording device is known to the computer. The image processor automatically detects at least one body region, and automatically suggests a scan area on the screen that covers this body region.

In an embodiment the image processor can detect at least two different body regions, preferably all body regions located on the image of the patient, with a scan area being automatically suggested and indicated for each body region.

Corresponding to the method described above, this device can include a selection unit (preferably predefined menu selection fields or buttons) that determine at least one scan area by selection of a body region with the selection unit. Thus, for example, by simply pressing the button "head" or "abdomen," the corresponding scan area is selected by the image processor and is displayed on the monitor of the system and the scan is correspondingly implemented.

In spite of this automatic process a manual correction unit for changing the scan area suggested by the image processor can be included. In such a case the suggested scan area (which is mostly bordered by simple lines) can be modified by the operating personnel by corresponding mouse clicks and subsequent movement of this line.

If the positioning ensues in a number of planes (i.e. 3-dimensionally), it is necessary to provide at least two image-recording devices with respective recording axes that are independent from one another, preferably orthogonal to one another. For each movement plane of the patient bed, an image-recording device with a recording axis preferably arranged perpendicular to this movement plane, can be provided.

In a further embodiment of the inventive device, the image-recording device can also be a 3D scanner, preferably a laser scanner or a 3D CMOS sensor, such that the patient image displayed on the screen enables a spatial representation. A display for spatial representation of the scan area also is provided.

The functioning of the inventive device primarily ensues via a program or program module that can be integrated into the existing apparatus (in terms of programming) of a diagnosis device or therapy device.

DESCRIPTION OF THE PREFERRED EMBODIMENTS

Figure 1:
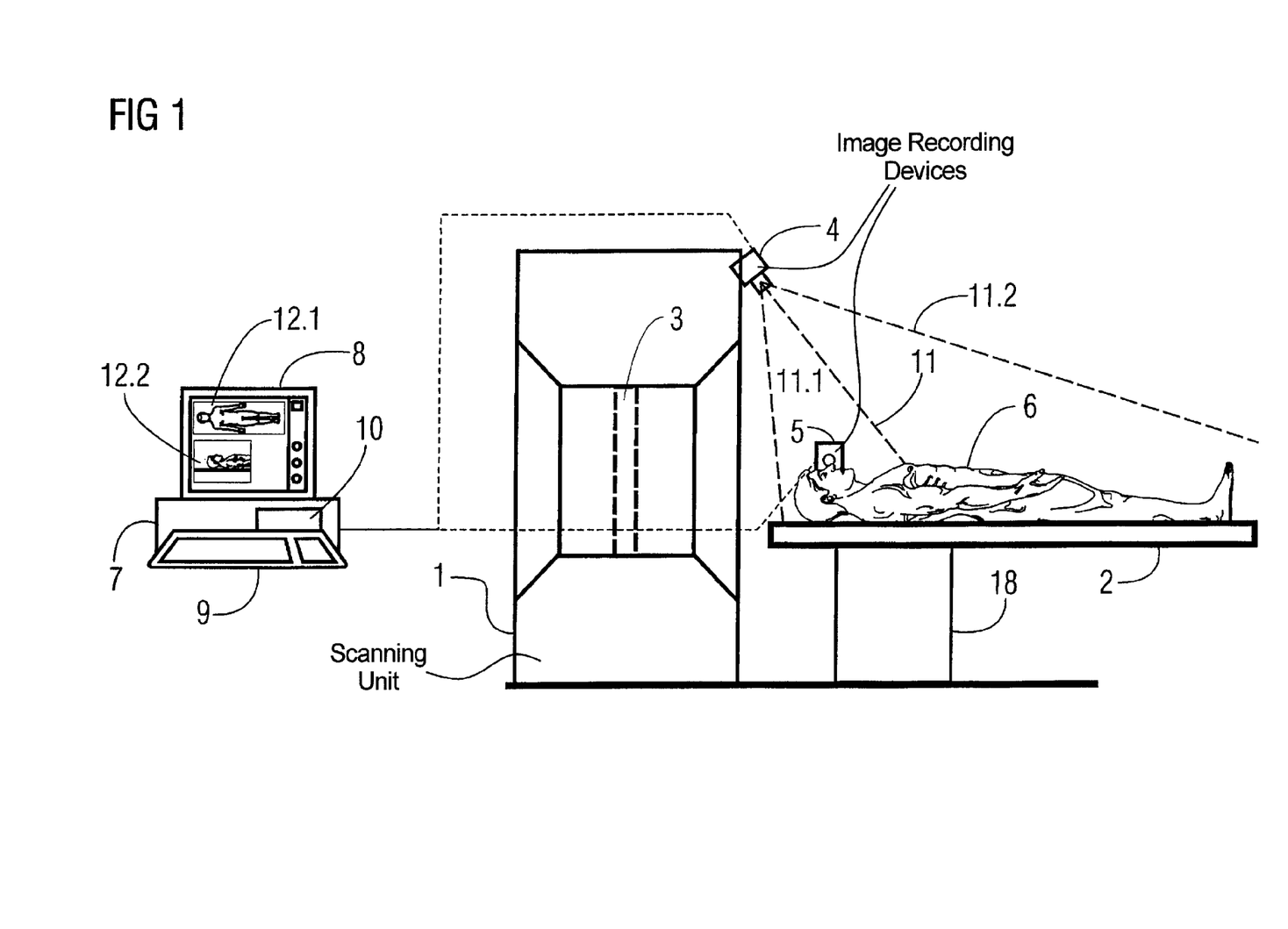
FIG. 1 shows a computed tomography apparatus according to the invention with a patient in side view.

FIG. 1 shows a side view of a computed tomography apparatus having a scanning unit 1 (gantry), with a bed 2 that can be moved into the scanning unit 1, and a computer 7 that is responsible for the evaluation and control of the computed tomography apparatus.

The computer 7 has an input keyboard 9, a screen 8, and a storage 10. The images obtained by the recording of the video cameras 4 and 5 are shown in the image sections 12.1 and 12.2 on the screen 8. The video camera 4 is arranged above the patient and provides a frontal image of the patient, while the video camera 5 is arranged laterally to the patient and correspondingly provides a lateral image of the head/chest area of the patient.

The patient bed 2 is arranged on a movement device 18 that is controlled by the computer 7 in order to appropriately insert the patient on the bed 2 into the scanning unit 1. It should be noted that, for clarity, only the dashed displayed connections between the video cameras 4 and 5 and the computer 7 are shown. Other control and data connections between the scanning unit 1, the movement device 18, and the computer 7 have been omitted for clarity of the drawings.

The inventive method is illustrated in a series of method steps, by means of FIGS. 2 through 5 that show the computed tomograph of FIG. 1 in a top view.

Figure 2:
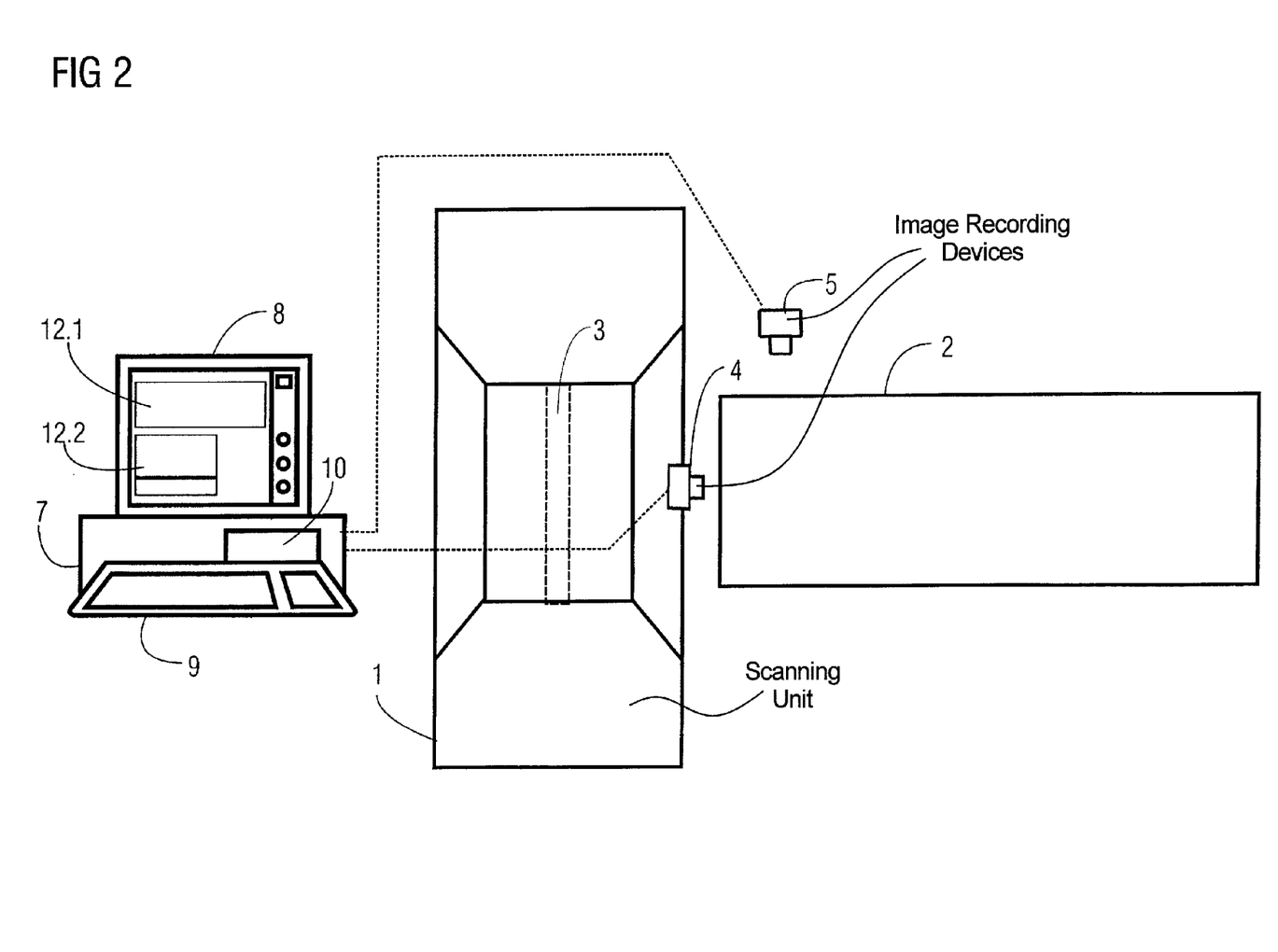
FIG. 2 shows a computed tomography apparatus according to the invention in top view with an empty bed.

FIG. 2 shows the computed tomography apparatus with an empty patient bed 2, the laterally arranged video camera 5, and the video camera 4 arranged above the patient bed 2. In this situation, both cameras 4 and 5 can record an empty image of their respective fields of view, and these are saved this in the computer 7 in the memory 10.

Figure 3:
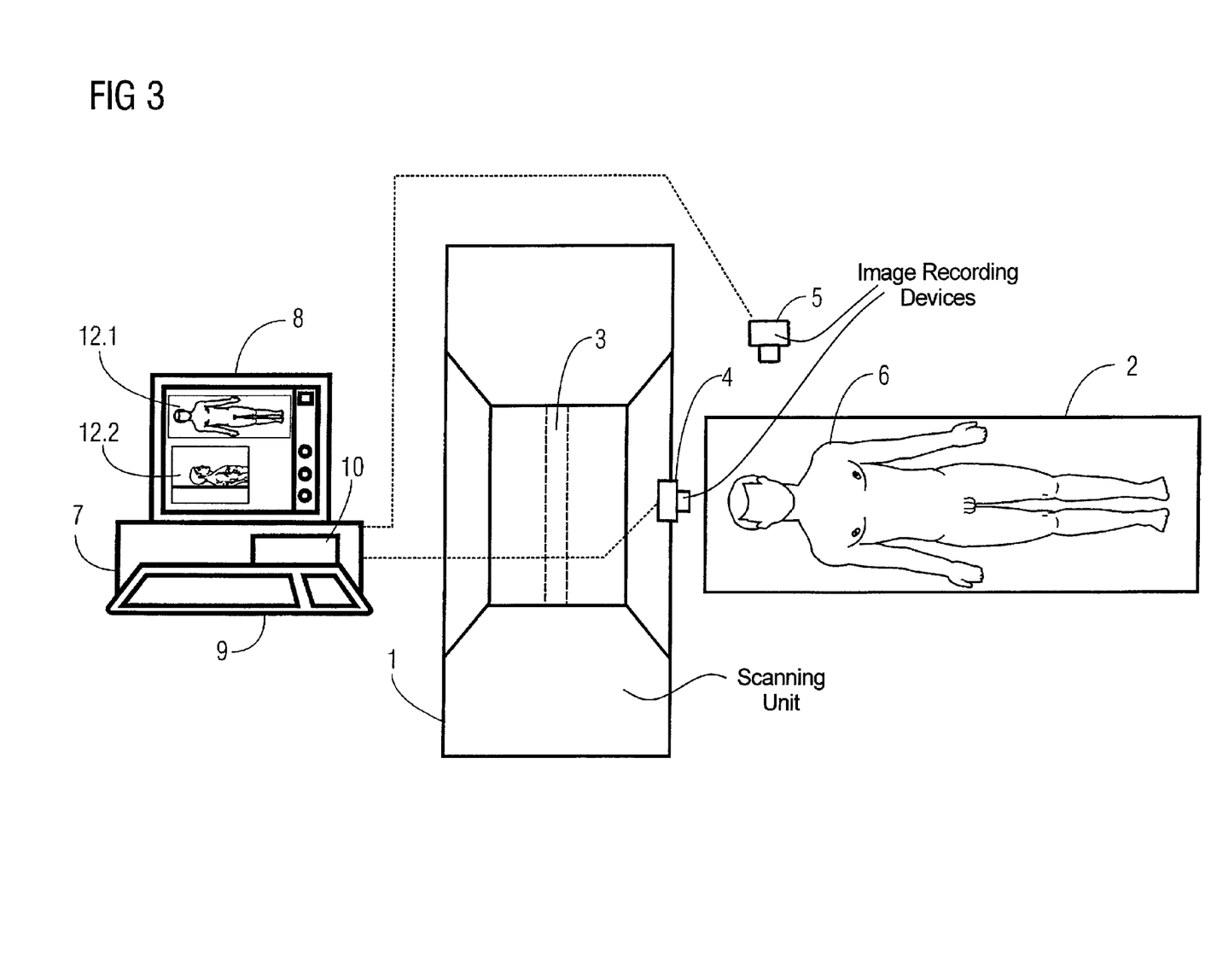
FIG. 3 shows a computed tomography apparatus according to the invention in top view with a patient.

The patient 6 subsequently lies on the patient bed 2, here in dorsal position (as is shown in FIG. 3), and occupies a specific position that can be, for example, such that the legs are slightly splayed and the hands are balled into fists in order to later achieve a better edge detection. The bed 2 occupied by the patient 6 is now imaged by the two video cameras 4 and 5, and simultaneously the saved empty image is subtracted from the actual image, such that only the difference between the empty image and the actual image remains as image information, i.e. only the patient is perceived in this subtraction image.

Figure 4:
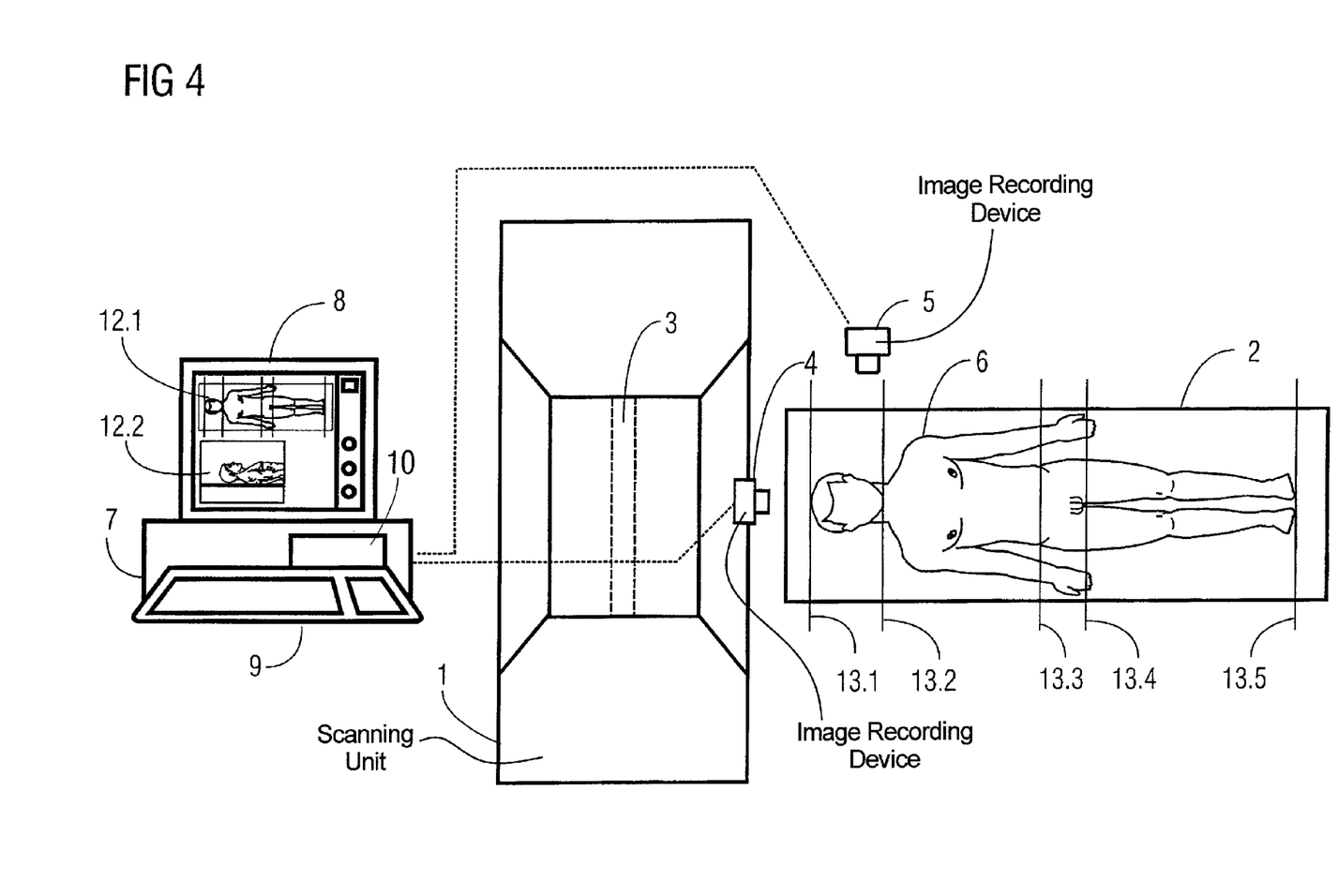
FIG. 4 shows a computed tomography apparatus according to the invention in a top view with automatically determined border lines.

In the next step, the actual image analysis of the remaining subtraction image of the patient now begins in the computer 7. A program loaded in the computer 7 analyzes the geometric attribute of the patient so that, for example, appropriate border lines 13.1 through 13.5 (as shown in FIG. 4) can be determined. As examples, the border lines 13.1 as the upper end of the head and 13.2 as the lower end of the head are shown. The line 13.3 defines the area of the hips, while the border line 13.4 identifies the area of the pubic bone and the border line 13.5 marks the ends of the feet.

Figure 5:
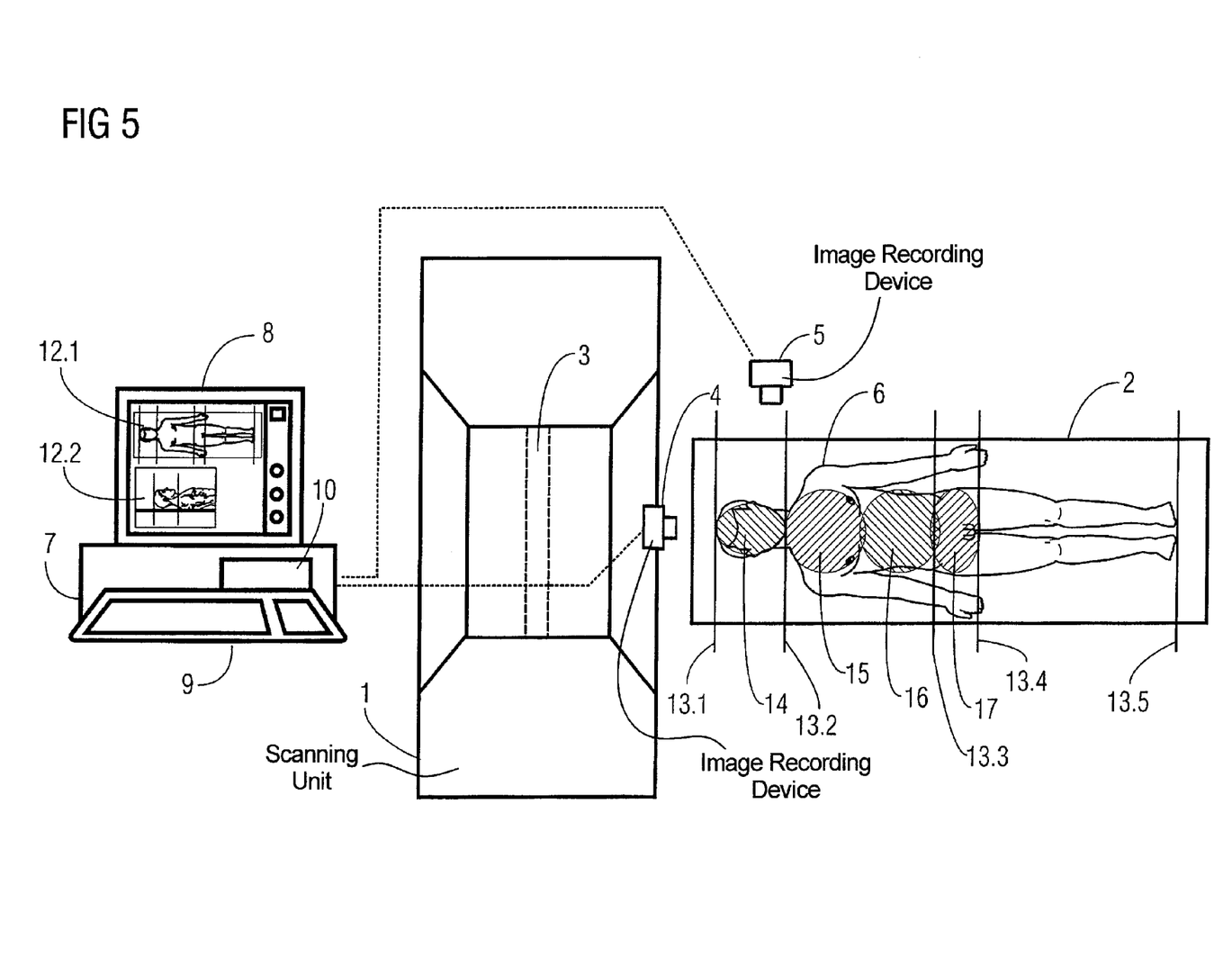
FIG. 5 shows a computed tomography apparatus according to the invention in a top view with detected body regions.

Corresponding to these border lines, an arrangement in the corresponding body regions can now be undertaken on the basis of known and statistically determined proportions. FIG. 5 shows the result of the analysis in the hatched regions 14 through 17, corresponding to the individual body regions: head, thorax, abdomen, and trunk. For better viewing, these body regions 14 through 17 are additionally displayed directly on the patient. In the actual embodiment these regions are, however, shown only on the screen 8. The same is true for the indicated border lines 13.1 through 13.5.

Figure 6:
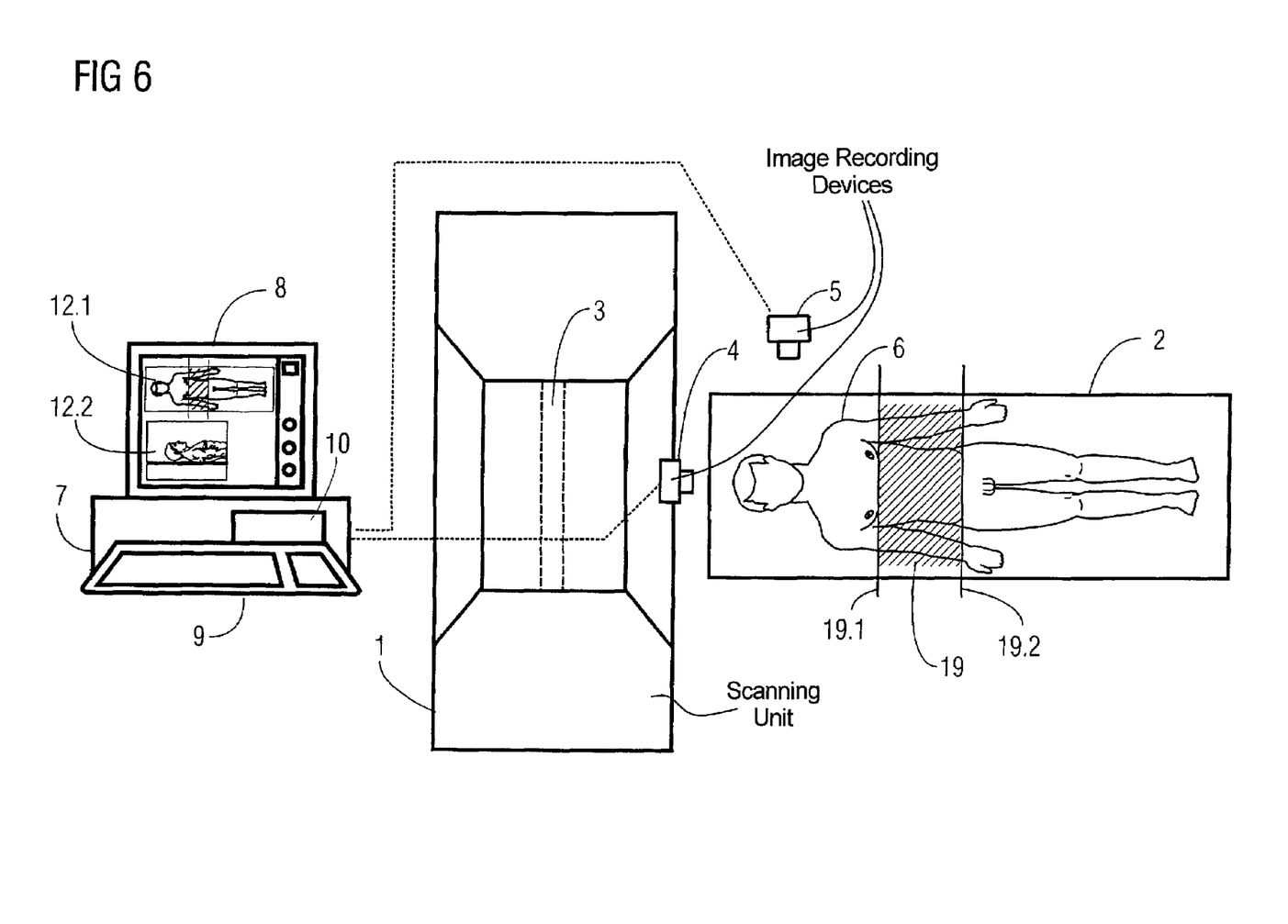
FIG. 6 shows a computed tomography apparatus according to the invention in a top view with a suggested scan area.

The operating personnel are able to select one or more body regions by simple operation of a key or by clicking in a screen menu, and the body region or body regions are subsequently marked by the computer 7 as scan area 19 with the boundaries 19.1 and 19.2, as shown in FIG. 6. Since the computer 7 "knows" the spatial correlation between the video cameras 4 and 5, it can automatically insert the patient into the scanning unit, such that the pre-selected body region(s) (here the abdomen) can be correspondingly scanned.

In a variant of the method, the desired body region to be imaged is specified before the implementation of the image analysis on the input device 9, or is determined via an appropriate menu or a key, such that the computer 7 subsequently searches only the predetermined body region in the image of the patient, and subsequently this is shown as the possible scan region.

Furthermore, there is also the possibility—after the automatic definition of the area to be scanned—to manually adjust and thereby to correct the borders 19.1 and 19.2 of the scan area via appropriate input devices, for example a mouse or a joystick or a touch screen.

It should be noted that the laterally mounted video camera 5 primarily serves to adjust the correct height position of the patient in relation to the rotational center of the detector. This can ensue purely manually or by means of an automatic image analysis, however the acquired information about the contours of the patient can also additionally be used to determine the individual body regions with better precision.

Furthermore, it should be noted that a three dimensional contour scanner can be undertaken instead of one or more video cameras, for example with a laser scanner, preferably with a 3D CMOS sensor, such that a corresponding spatial display can be shown on the screen 8, whereby the detection of individual body regions can be additionally improved via a spatial imaging of the patient.

The inventive method and device can be used not only with an x-ray computed tomography apparatus, but also with magnetic resonance tomography systems, angiography devices, ultrasound therapy devices, or radiation therapy devices.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for positioning a patient in a medical device having a treatment unit configured to receive a patient therein, a computer, and a patient bed, configured to receive a patient thereon, movable in at least one plane relative to said treatment unit, said method comprising the steps of:

prior to obtaining medical diagnostic data from the patient with said treatment unit, acquiring, with a non-invasive image-recording device, an empty image of the bed surface with no patient thereon, and acquiring an actual, non-invasive image of of the bed surface with the patient on the patient bed showing the bed surface and the exterior of the patient, and subtracting said empty image from said actual image to obtain a subtraction image showing only the exterior of the patient, and displaying said subtraction image on a display screen connected to said computer;

providing information to said computer identifying a spatial correlation between a coordinate system of the treatment unit and said image-recording device; and an exterior by executing an image processing program in said computer, detecting an exterior body region of the patient by analyzing said subtraction image to identify geometry of the exterior of the patient in the subtraction image and comparing the geometry to known and statistically determined proportions of exterior human anatomy and automatically, based on a result of executing said image processing program, displaying a suggested scan area, from which to subsequently obtain said medical diagnostic data from the scan area using said treatment unit, in said subtraction image on said display screen that covers said body region.

2. A method as claimed in claim 1 comprising, in said image processing program, detecting two different body regions of the patient by analyzing said subtraction image and, for each of said different body regions, and automatically displaying a suggested scan area in said subtraction image on said display screen that covers that body region.

3. A method as claimed in claim 1 comprising optically emphasizing the detected body region on said display screen.

4. A method as claimed in claim 1 comprising manually entering a designation into said computer of said body region to be detected by said image processing program.

5. A method as claimed in claim 4 comprising entering said designation of said body region to be detected into said computer using a displayed menu.

6. A method as claimed in claim 4 comprising entering said designation of said body region to be detected into said computer by operating a keypad connected to said computer.

7. A method as claimed in claim 4 comprising allowing selection by a user of multiple body regions to be detected simultaneously.

8. A method as claimed in claim 1 comprising allowing manual alteration of the suggested scan area displayed on said display screen by said image processing program.

9. A method as claimed in claim 1 comprising designating said suggested scan area on said display screen with two lines respectively disposed at edges of said suggested scan area.

10. A method as claimed in claim 9 comprising designating said suggested scan area on said display screen with two parallel lines at the respective edges of the suggested scan area.

11. A method as claimed in claim 1 wherein said non-invasive image-recording device is a first non-invasive image-recording device and wherein said empty image is a first empty image, and said actual, non-invasive image is a first, non-invasive actual image, and said subtraction image is a first subtraction image, and comprising the additional steps of:
   prior to obtaining medical diagnostic data from the patient with said treatment unit, acquiring a second empty image of the bed surface with no patient thereon and acquiring a second actual, non-invasive image of the bed surface with the patient on the patient bed with a second non-invasive image-recording device showing the bed surface and the exterior of the patient, from a recording axis that is independent of a recording axis of said first non-invasive image-recording device, and subtracting said second empty image from said second actual image to obtain a second subtraction image showing only the exterior of the patient, and also displaying said second subtraction image on said computer;
   providing information to said computer identifying a spatial correlation between the coordinate system of the treatment unit and said second image-recording device; and
   with said image processing program in said computer, displaying said suggested scan area in each of said first and second subtraction images.

12. A method as claimed in claim 11 comprising disposing said first and second non-invasive image-recording devices relative to each other with the respective recording axes thereof being orthogonal to each other.

13. A method as claimed in claim 11 wherein said patient bed is movable in a plurality of movement planes relative to said treatment unit, and comprising the additional steps of:
   for each movement plane, acquiring said first and second actual images the patient on the patient bed in that movement plane;
   providing information to said computer identifying a spatial correlation in that movement plane between the coordinate system of the treatment unit and each of said first and second non-invasive image-recording devices; and
   with said image processing program displaying said suggested scan area in each of said subtraction images on said display screen.

14. An arrangement for positioning a patient in a medical device having a treatment unit adapted to receive a patient therein, and a patient bed, having a bed surface configured to receive a patient thereon, movable in at least one plane relative to said treatment unit, said arrangement comprising:
   a computer;
   a non-invasive image-recording device that acquires an empty image of the patient bed with no patient thereon prior to obtaining medical diagnostic data from the patient with said treatment unit, and that acquires, also showing only the exterior of the patient, an actual, non-invasive image of the patient bed and the patient on the patient bed showing the bed surface and the exterior of the patient, and that subtracts said empty image from said actual image to obtain a subtraction image showing only the exterior of the patient, and that displays said subtraction image on a display screen connected to said computer;
   said computer containing information identifying a spatial correlation between a coordinate system of the treatment unit and said image-recording device; and
   said computer detecting an exterior body region of the patient by analyzing said image to identify exterior geometry of the patient in the subtraction image and comparing the geometry to known and statistically determined proportions of exterior human anatomy and said computer, based on a result of executing said image processing program, automatically displaying a suggested scan area in said subtraction image on said display screen that covers said body region, from which to subsequently obtain said medical diagnostic data from the scan area using said treatment unit.

15. An arrangement as claimed in claim 14 wherein said computer detects two different body regions of the patient by analyzing said image and, for each of said different body regions, automatically displays a suggested scan area in said subtraction image on said display screen that covers that body region.

16. An arrangement as claimed in claim 14 wherein said computer optically emphasizes the detected body region on said display screen.

17. An arrangement as claimed in claim 14 comprising an input unit allowing manual entry of a designation into said computer of said body region to be detected by said computer.

18. An arrangement as claimed in claim 17 wherein said input unit is a displayed menu.

19. An arrangement as claimed in claim 17 wherein said input unit is a keypad connected to said computer.

20. An arrangement as claimed in claim 17 wherein said input unit allows selection by a user of multiple body regions to be detected simultaneously.

21. An arrangement as claimed in claim 14 comprising an input unit allowing manual alteration of the suggested scan area displayed on said display screen by said computer.

22. An arrangement as claimed in claim 14 wherein said computer designates said suggested scan area on said display screen with two lines respectively disposed at edges of said suggested scan area.

23. An arrangement as claimed in claim 22 wherein said computer designates said suggested scan area on said display screen with two parallel lines at the respective edges of the suggested scan area.

24. An arrangement as claimed in claim 14 wherein said non-invasive image-recording device is a first non-invasive image-recording device and wherein said actual, non-invasive image is a first actual, non-invasive image, and said subtraction image is a first subtraction image, and comprising:
   a second non-invasive image recording device that acquires, prior to obtaining medical diagnostic data from the patient with said treatment unit, a second empty image of the bed surface with no patient thereon, and that acquires, also prior to obtaining medical diagnostic data from the patient with said treatment unit, a second actual, non-invasive image of the bed surface with the patient on the patient bed showing the bed surface and the exterior of the patient, said second non-invasive image recording device having a recording axis that is independent of a recording axis of said first non-invasive image-recording device, and said computer subtracting said second empty image from said second actual image to obtain a second subtraction image, and causing said second subtraction image to be displayed on said display screen connected to said computer;

said computer containing information identifying a spatial correlation between the coordinate system of the treatment unit and said second non-invasive image-recording device; and said computer causing said suggested scan area to be displayed in each of said first and second subtraction images.

25. An arrangement as claimed in claim 24 wherein said first and second non-invasive image-recording devices are disposed relative to each other with the respective recording axes thereof being orthogonal to each other.

26. An arrangement as claimed in claim 24 wherein said patient bed is movable in a plurality of movement planes relative to said treatment unit, and comprising the additional steps of:

for each movement plane, said first and second non-invasive image recording devices respectively acquiring said first and second actual, non-invasive images with the patient on the patient bed in that movement plane;

and said computer containing information identifying a spatial correlation in that movement plane between the coordinate system of the treatment unit and each of said first and second non-invasive image-recording devices; and said computer said suggested scan area to be displayed in each of said subtraction images on said display screen.

* * * * *